US00PP22270P2

(12) United States Plant Patent
Kabbes

(10) Patent No.: US PP22,270 P2
(45) Date of Patent: Nov. 22, 2011

(54) ***GERANIUM* PLANT NAMED 'EUREKA BLUE'**

(50) Latin Name: ***Geranium* hybrid**
Varietal Denomination: Eureka Blue

(75) Inventor: Brian Kabbes, Suameer (NL)

(73) Assignee: Stephen Page, Oude Wetering (NL)

( * ) Notice: Subject to any disclaimer, the term of this patent is extended or adjusted under 35 U.S.C. 154(b) by 0 days.

(21) Appl. No.: 12/931,625

(22) Filed: Feb. 3, 2011

(51) Int. Cl.
*A01H 5/00* (2006.01)

(52) U.S. Cl. ..... Plt./324

(58) Field of Classification Search ..... Plt./331, Plt./324
See application file for complete search history.

(56) References Cited

U.S. PATENT DOCUMENTS

PP12,148 P2 * 10/2001 van Noort ..... Plt./324
PP16,305 P2 * 3/2006 Bremner ..... Plt./324

* cited by examiner

*Primary Examiner* — Wendy C Haas
(74) *Attorney, Agent, or Firm* — C. A. Whealy

(57) ABSTRACT

A new and distinct cultivar of *Geranium* plant named 'Eureka Blue', characterized by its upright and outwardly spreading plant habit; vigorous growth habit; freely branching habit; freely flowering habit; large violet blue-colored flowers with purple-colored venation and white-colored centers; long and continuous flowering period; and good garden performance.

1 Drawing Sheet

Botanical designation: *Geranium* hybrid.
Cultivar denomination: 'EUREKA BLUE'.

BACKGROUND OF THE INVENTION

The present invention relates to a new and distinct cultivar of *Geranium* plant, botanically known as *Geranium* hybrid and hereinafter referred to by the name 'Eureka Blue'.

The new *Geranium* plant is a product of a planned breeding program conducted by the Inventor in Suameer, The Netherlands. The objective of the breeding program is to create new vigorous *Geranium* plants with numerous large flowers and long flowering period.

The new *Geranium* plant originated from a cross-pollination made by the Inventor in May, 2001 in Suameer, The Netherlands of a seedling selection of *Geranium* hybrid identified as code number 2002/3, not patented, as the female, or seed, parent with a seedling selection of *Geranium* hybrid identified as code number 2001/16, not patented, as the male, or pollen, parent. The new *Geranium* plant was discovered and selected by the Inventor as a single flowering plant within the progeny of the stated cross-pollination in a controlled environment in Suameer, The Netherlands in June, 2002.

Asexual reproduction of the new *Geranium* plant by cuttings in a controlled environment in Suameer, The Netherlands since January, 2003, has shown that the unique features of this new *Geranium* plant are stable and reproduced true to type in successive generations.

SUMMARY OF THE INVENTION

Plants of the new *Geranium* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Eureka Blue'.

These characteristics in combination distinguish 'Eureka Blue' as a new and distinct *Geranium* plant:

1. Upright and outwardly spreading plant habit.
2. Vigorous growth habit.
3. Freely branching habit.
4. Freely flowering habit.
5. Large violet blue-colored flowers with purple-colored venation and white-colored centers.
6. Long and continuous flowering period.
7. Good garden performance.

Plants of the new *Geranium* differ primarily from plants of the female parent selection in the following characteristics:

1. Plants of the new *Geranium* are larger than plants of the female parent selection.
2. Plants of the new *Geranium* have larger leaves than plants of the female parent selection.
3. Plants of the new *Geranium* have larger flowers than plants of the female parent selection.

Plants of the new *Geranium* differ primarily from plants of the male parent selections in the following characteristics:

1. Plants of the new *Geranium* are larger than plants of the male parent selection.
2. Plants of the new *Geranium* have larger leaves than plants of the male parent selection.
3. Plants of the new *Geranium* have larger flowers than plants of the male parent selection.

Plants of the new *Geranium* can be compared to plants of *Geranium* 'Johnson's Blue', not patented. In side-by-side comparisons conducted in Suameer, The Netherlands, plants of the new *Geranium* differed primarily from plants of 'Johnson's Blue' in the following characteristics:

1. Plants of the new *Geranium* were larger than plants of 'Johnson's Blue'.
2. Plants of the new *Geranium* had larger leaves than plants of 'Johnson's Blue'.
3. Plants of the new *Geranium* had larger flowers than plants of 'Johnson's Blue'.

Plants of the new *Geranium* can also be compared to plants of *Geranium* 'Brookside', not patented. In side-by-side comparisons conducted in Suameer, The Netherlands, plants of the new *Geranium* differed primarily from plants of 'Brookside' in the following characteristics:

1. Plants of the new *Geranium* were larger than plants of 'Brookside'.
2. Plants of the new *Geranium* had larger leaves than plants of 'Brookside'.
3. Plants of the new *Geranium* had larger flowers than plants of 'Brookside'.

BRIEF DESCRIPTION OF THE PHOTOGRAPHS

The accompanying colored photographs illustrate the overall appearance of the new *Geranium* plant showing the colors as true as it is reasonably possible to obtain in colored reproductions of this type. Colors in the photographs may differ slightly from the color values cited in the detailed botanical description which accurately describe the colors of the new *Geranium* plant.

The photograph at the bottom of the sheet comprises a side perspective view of a typical flowering plant of 'Eureka Blue' grown in a container.

The photograph at the top of the sheet is a close-up view of a typical flower of 'Eureka Blue'.

DETAILED BOTANICAL DESCRIPTION

The aforementioned photographs and following observations, measurements and values describe plants grown during the autumn and winter in one-gallon containers in a polyethylene-covered greenhouse in Lancaster, Pa. During the production of the plants, day temperatures ranged from 21° C. to 29° C. and night temperatures averaged 18° C. Plants were ten months old when the photographs and the description were taken. In the detailed description, color references are made to The Royal Horticultural Society Colour Chart, 2007 Edition, except where general terms of ordinary dictionary significance are used.

Botanical classification: *Geranium* hybrid 'Eureka Blue'.

Parentage:

*Female, or seed, parent.*—Seedling selection of *Geranium* hybrid identified as code number 2002/3, not patented.

*Male, or pollen, parent.*—Seedling selection of *Geranium* hybrid identified as code number 2001/16, not patented.

Propagation:

*Type.*—By cuttings.

*Time to initiate roots, summer.*—About seven to ten days at 20° C.

*Time to initiate roots, winter.*—About two to three weeks at 20° C.

*Time to produce a rooted young plant, summer.*—About eight weeks at 20° C.

*Time to produce a rooted young plant, winter.*—About 16 weeks at 20° C.

*Root description.*—Medium in thickness, fibrous; brown in color.

*Rooting habit.*—Moderate branching; medium density.

Plant description:

*Plant and growth habit.*—Hardy herbaceous perennial; upright and outwardly spreading plant habit; vigorous growth habit.

*Plant height.*—About 32 cm.

*Plant width.*—About 48 cm by 56 cm.

*Branching habit.*—Freely branching habit with about 14 lateral branches per plant.

*Lateral branch length.*—About 27 cm.

*Lateral branch diameter.*—About 4 mm.

*Internode length.*—About 1.5 cm to 9 cm.

*Lateral branch aspect.*—Outwardly and horizontally spreading.

*Lateral branch strength.*—Strong.

*Lateral branch texture.*—Pubescent.

*Lateral branch color.*—Close to 199D tinged with close to 182B.

Foliage description:

*Arrangement.*—Opposite, simple.

*Length.*—About 5.8 cm.

*Width.*—About 6.4 cm.

*Shape.*—Deeply dissected.

*Apex.*—Acute.

*Base.*—Sagittate.

*Margin.*—Five palmate lobes; lobes biserrate.

*Venation pattern.*—Palmate; reticulate.

*Texture, upper and lower surfaces.*—Pubescent.

*Color.*—Developing leaves, upper surface: Close to N137C. Developing leaves, lower surface: Close to 147B. Fully developed leaves, upper surface: Close to N137A to N137B; venation, close to 137B. Fully developed leaves, lower surface: Close to 147B; venation, close to 147B.

*Petiole.*—Length: About 20.5 cm. Diameter: About 2 mm. Texture, upper and lower surfaces: Pubescent. Color, upper and lower surfaces: Close to 195A.

Flower description:

*Flowering habit.*—Single rotate flowers arranged in clusters; flowers axillary; freely flowering habit with about 30 flowers per plant.

*Fragrance.*—None detected.

*Flowering season and flower longevity.*—In The Netherlands, flowering is continuous from late April to late June; individual flowers last about three to three days on the plant; corollas not persistent, however sepals and gynoecium are persistent.

*Flower bud length.*—About 2 cm.

*Flower bud diameter.*—About 9 mm.

*Flower bud shape.*—Ovoid.

*Flower bud color.*—Close to 83A.

*Flower diameter.*—About 3.1 cm.

*Flower height.*—About 1.5 cm.

*Petals.*—Quantity per flower: Five in a single whorl. Length: About 2 cm. Width: About 1.5 cm. Shape: Obovate. Apex: Rounded. Base: Acute. Margin: Entire. Texture, upper and lower surfaces: Smooth, glabrous; velvety. Color: When opening, upper and lower surfaces: Close to 93A. Fully opened, upper surface: Close to N89A; towards the base, close to NN155C; venation, close to N79C. Fully opened, lower surface: Close to N88A.

*Sepals.*—Quantity per flower: Five, arranged in a single whorl. Length: About 1.4 cm. Diameter: About 4 mm. Shape: Narrowly elliptical. Apex: Acuminate. Base: Truncate. Margin: Entire. Texture, upper surface: Smooth, glabrous. Texture, lower surface: Pubescent. Color, upper and lower surfaces: Close to 146B.

*Peduncles.*—Length: About 14.6 cm. Diameter: About 1 mm. Aspect: About 30° to 45° from the stem axis. Strength: Strong. Texture: Pubescent. Color: Close to 148A.

*Pedicels.*—Length: About 1.4 cm. Diameter: About 1 mm. Aspect: About 30° from the stem axis. Strength: Strong. Texture: Pubescent. Color: Close to 148A.

*Reproductive organs.*—Androecium: Stamen quantity per flower: About ten. Filament length: About 8 mm. Filament color: Close to 157A to 157B. Anther length: About 2 mm. Anther shape: Lanceolate. Anther color: Close to N92B. Pollen amount: Scarce. Pollen color: Close to 146C. Gynoecium: Pistil quantity per flower: One. Pistil length: About 1 cm. Stigma shape: Five-parted and recurving. Stigma color: Close to 86A. Style length: About 6 mm. Style color: Close to 199C to 199D. Ovary color: Close to 148B.

*Seed/fruits.*—Seed and fruit development have not been observed.

Disease/pest resistance: Plants of the new *Geranium* have been not been observed to be resistant to pathogens and pests common to *Geraniums.*

Garden performance: Plants of the new *Geranium* have been observed to have good garden performance and to tolerate rain, wind and to be hardy to USDA Zone 5.

It is claimed:

1. A new and distinct *Geranium* plant named 'Eureka Blue' as illustrated and described.

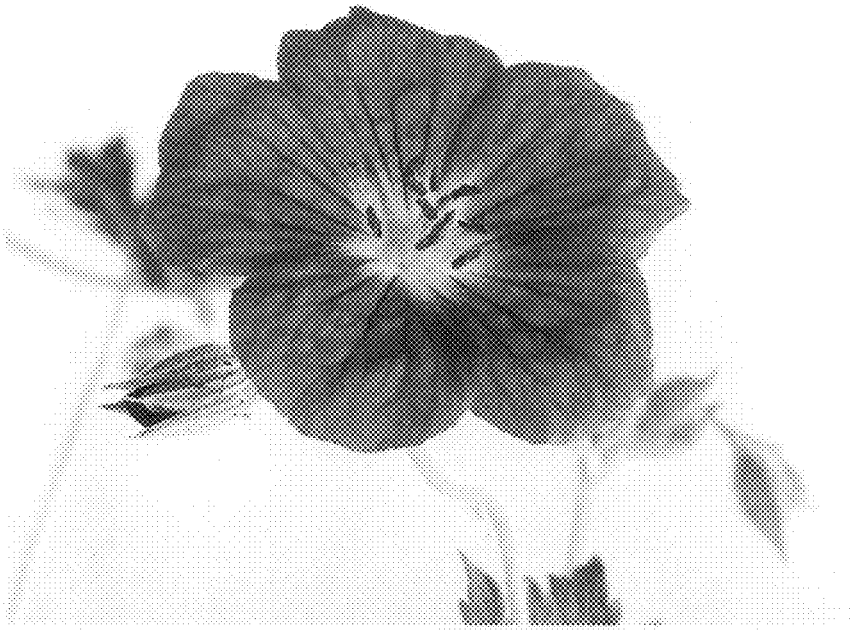
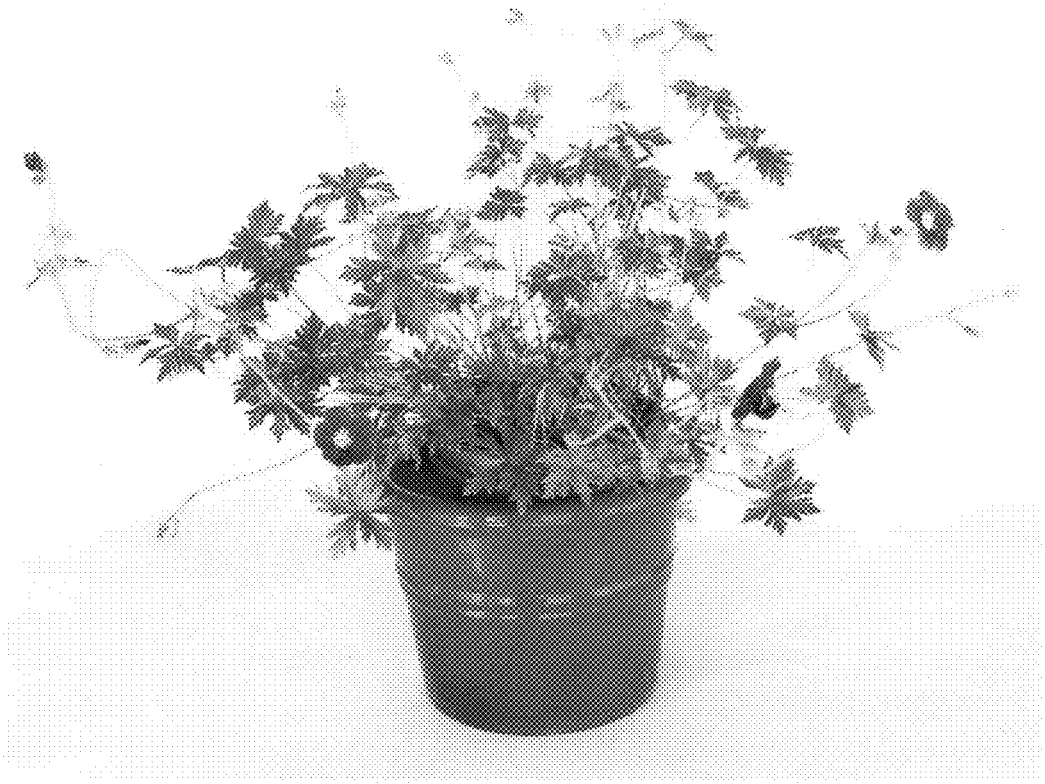

* * * * *